United States Patent [19]
Jansen

[11] Patent Number: 5,376,115
[45] Date of Patent: Dec. 27, 1994

[54] INTRAOCULAR LENS WITH VAULTING HAPTIC

[75] Inventor: Peter Jansen, Uithuizen, Netherlands

[73] Assignee: Pharmacia AB, Upsala, Sweden

[21] Appl. No.: 99,333

[22] Filed: Aug. 2, 1993

[51] Int. Cl.⁵ .............................................. A61F 2/16
[52] U.S. Cl. ..................................................... 623/6
[58] Field of Search ............................... 623/6

[56] References Cited

U.S. PATENT DOCUMENTS

| | | | |
|---|---|---|---|
| 4,244,060 | 1/1981 | Hoffer | 623/6 |
| 4,573,998 | 3/1986 | Mazzocco | 623/6 |
| 4,648,878 | 3/1987 | Kelman | 623/6 |
| 4,702,244 | 10/1987 | Mazzocco | 623/6 |
| 4,863,465 | 9/1989 | Kelman | 623/6 |
| 4,871,362 | 10/1989 | Nurmamedov | 623/6 |
| 4,990,159 | 2/1991 | Kraff | 623/6 |
| 5,071,432 | 12/1991 | Baikoff | 623/6 |

Primary Examiner—Randall Green
Assistant Examiner—Mary Beth Jones

[57] ABSTRACT

An intraocular lens that includes an optical lens body and haptics extending outwardly from the optical lens, said haptics extending at about a zero degree of angulation with respect to the lens body when not under compression and at least one haptic having at least one segment which is formed so that upon compression of the haptics under conditions similar to implantation said at least one segment will create a torque which causes the lens to vault in only one predetermined direction and to a predetermined angulation greater than zero.

7 Claims, 4 Drawing Sheets

INTRAOCULAR LENS WITH VAULTING HAPTIC

The present invention is related to the field of ophthalmology and more specifically to new intraocular lenses which have been found to considerably facilitate and improve the result of IOL implantation through a small incision.

BACKGROUND

A most common age related observation is that the visual acuity is reduced since the lens of the eye has become cloudy making the vision blurred. This opacification of the lens is called cataract and is caused by molecular rearrangement of the lens components with increased light-scattering. Some cataracts furthermore develop a yellow-brown colour due to pigment deposition which also contributes to reduction of vision.

Besides the most frequent cataracts, which occur in elderly people, the lens might also be affected due to diabetes or numerous types of injuries.

The only treatment of cataracts available is to remove the cloudy lens through surgery. Once the lens has been removed a new artificial lens is required so that the eye can focus clearly. There are three methods of restoring vision after cataract surgery: by cataract spectacles, by contact lenses or by implantation of intraocular lenses.

An intraocular lens implant is prepared from a biocompatible material, for instance polymethylmethacrylate (PMMA) or silicone, and is placed inside the eye by the surgeon in direct connection with the cataract removal.

Cataract surgery has changed dramatically over the past twenty years, principally as a result of introduction of the operating microscope, introduction of viscoelastic substances such as Healon ®, better instrumentation, improved surgical techniques and refinement of the intraocular lens implants as such. The state of the art methods are constantly being developed and improved.

Figure 1:
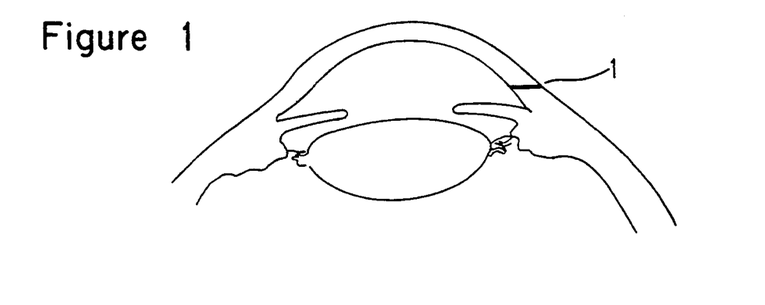
FIG. 1 shows making an incision in the cornea.
Figure 2:
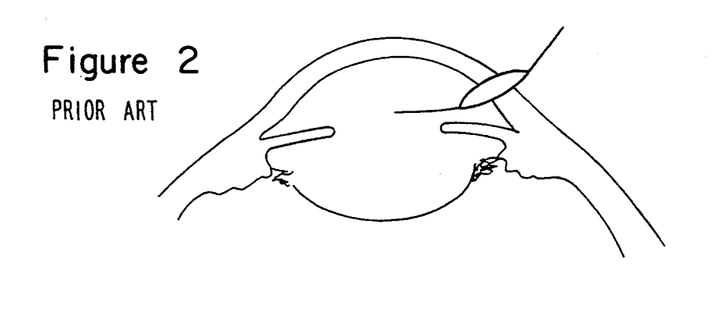
FIG. 2 shows inserting a conventional IOL through the incision.
Figure 3:
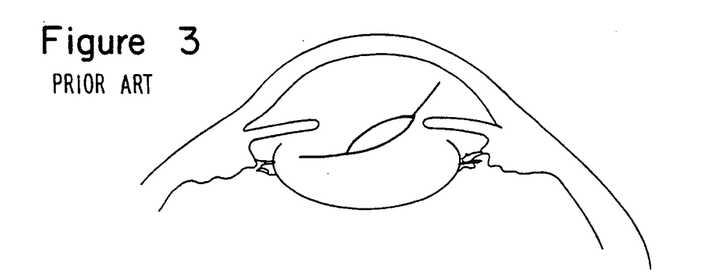
FIG. 3 shows manipulating a conventional IOL past the iris.
Figure 4:
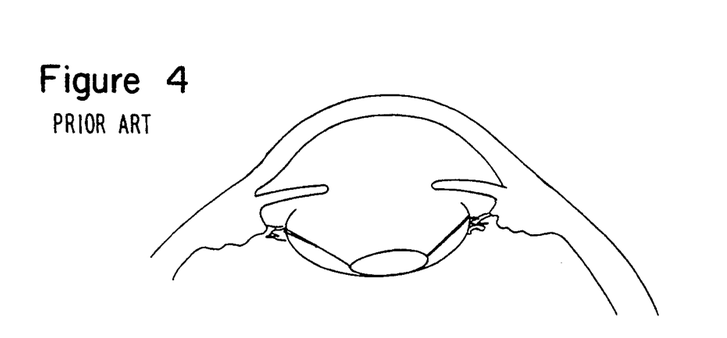
FIG. 4 shows a conventional IOL seated in the lens capsule.
Figure 5:
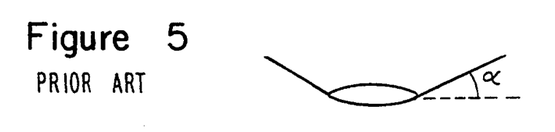
FIG. 5 shows a conventional IOL.

Heretofore most intraocular lens implantations have involved first making an incision (1) in the cornea as indicated in FIG. 1 and then filling the anterior segment of the eye with a viscoelastic material. After that an IOL is inserted through the incision (FIG. 2), manipulated past the iris (FIG. 3) and then seated closely adjacent the posterior wall of the lens capsule (FIG. 4). The IOL shown in FIGS. 2-4 has the two haptics attached to the lens at an angle α which is referred to as degree of angulation, which is shown in FIG. 5. This angle is often about 10 degrees.

A surgical method gaining in popularity is the phacoemulsification technique, that utilises ultrasonic vibrations to fragment the lens nucleus, thus allowing removal of the lens material through an incision that is approximately 3 mm long. The benefits of a small incision are faster visual rehabilitation, faster healing and less astigmatism than with conventional large incisions. A hollow titanium needle with a diameter of about 1 mm is activated to vibrate by a magnetostrictive ultrasonic mechanism. The mechanical vibrations transform the lens into an emulsion, hence the name phacoemulsification.

As the phacoemulsification technique has been refined the construction of the incision has developed to allow sealing of the wound without the need for sutures—"self sealing incisions".

Figure 6:
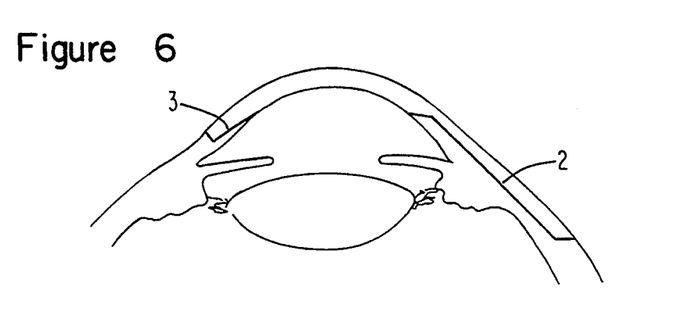
FIG. 6 shows a self-sealing incision.

Such a self sealing incision is based on the valve being constructed through an internal lip of corneal tissue that is pressed towards the outer part of the wound by the internal pressure in the eye (see FIG. 6). The valve can be made either entirely in the cornea, (3) ("clear cornea incision") or partly in the sclera (2) ("scleral tunnel incision"). The operation must be very accurately performed: for a corno-scleral tunnel the scleral incision is made 1-2.5 mm peripheral to limbus, that is the grey line separating the clear cornea from the white sclera. Using a knife with a rounded tip, a tunnel/valve is fashioned, about one half scleral depth and about 3 mm wide and 2 mm long. This is followed by the incision into the anterior chamber. Using a knife with a pointed tip the tunnel/valve is extended into the clear cornea another 1-2 mm with exactly the same careful precise motion. Following this procedure a very accurate valve construction is prepared. After removal of the opacified lens the incision is extended to the size required for the intraocular lens to be implanted, the anterior segment of the eye is filled with a viscoelastic material and the lens is implanted. Minimising the size of the lens during implantation is accordingly of great importance in order to allow the use of very small incisions, which are often referred to as tunnel incisions. The tunnel or small incision technique is described for instance in J Cataract Refract Surg 16(5) (1990) pp. 567–577 by Menapace, R. et al and in Ophthalmology (U.S.) 100(2) (1993) pp. 159–163 by Ormerod, L.D. et al.

A conventional incision (1) as shown in FIG. 1, which is closer to the limbus, and which enters the anterior chamber straight does not have the advantages discussed above. Tunnel incision offers, for reasons mentioned above, great advantages, out it is of crucial importance that lenses suitable for the procedure are available. In this connection considerable efforts have been made to develop a foldable lens which can be deformed during the insertion step but which after insertion in the eye returns to the predetermined size. This concept is disclosed in U.S. Pat. No. 4,702,244 and U.S. Pat. No. 4,573,998.

One specific problem in connection with tunnel incision implantation has been identified. When a conventional IOL, which as mentioned above has about a 10° angulation, is implanted through a tunnel incision, the lens enters the eye at a different angle (see FIG. 7) than when implanted through a regular incision in the cornea (see FIG. 1). The problem is that the leading loop (or haptic) of the introccular lens has an angulation of 10 degrees and during insertion there is a risk of its touching the inside of the cornea (see FIG. 7), which contains a layer of endothelial cells which are extremely sensitive to mechanical damage. The function of the endothelial cell layer is to allow the aqueous component into the cornea and to pump out excess fluid so that transparency is maintained. The pump is located in the cell membranes of the endothelium. The cells are hexagonal in shape and seem to be fitted together much as tiles on a floor. The hexagonal configuration minimises mechanical stress between units. Mechanical damage to the endothelial cells results in the mechanism described above being disturbed and can further cause cell death and if significant cell death occurs the cornea becomes edematous and opaque and corneal transplantation is required.

THE INVENTION

We have now developed a new concept for an intraocular lens so that there is less risk that the endothelium will be mechanically disturbed and which further reduces the need to manipulate the tunnel/valve construction during the implantation phase. Our intraocular lens includes an optical lens body and haptics extending outwardly from the optical lens and when said haptics are not under compression they extend at about a zero degree of angulation with respect to the lens body. At least one of the haptics has at least one segment which is formed so that upon compression of the haptics under conditions similar to implantation said at least one segment will create a torque which causes the lens to vault in only one predetermined direction and to a predetermined angulation greater than zero.

Figure 7:
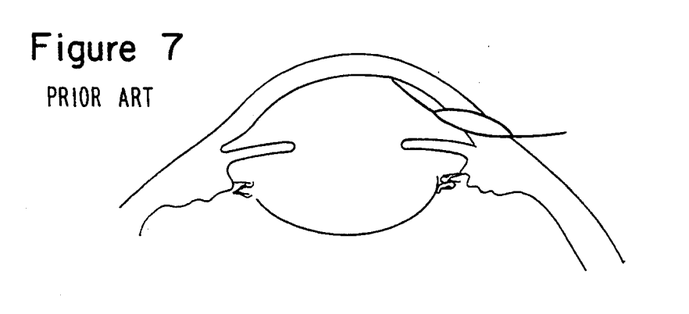
FIG. 7 shows insertion of a conventional IOL through an incision.
Figure 8:
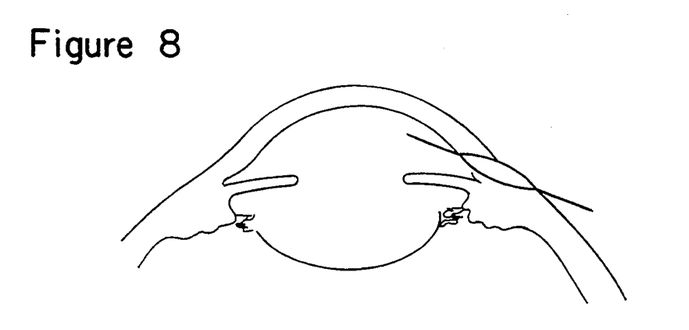
FIG. 8 shows insertion of an IOL according to the invention through a tunnel incision.
Figure 9:
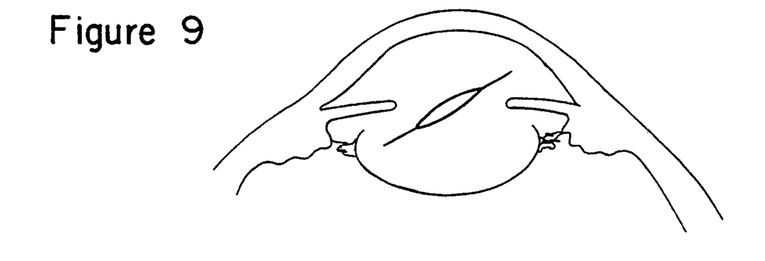
FIG. 9 shows manipulation of an IOL according to the invention past the iris.

Since the IOL according to our invention has about a zero degree of angulation when the haptics are not compressed, it is much easier to insert the IOL through a tunnel incision (see FIG. 8) and minimise the risk that the leading haptic will touch the inside of the cornea (i.e. contrast FIGS. 7 and 8). However, once our IOL is inserted through the incision and manoeuvred past the iris (see FIG. 9), it is necessary that the IOL "vault" from a planar position to the position shown in FIG. 10 so that the lens will contact or be closely adjacent to the posterior wall of the capsule. Contact between the lens and the posterior wall of the capsule is believed to play an important role in reducing the risk of secondary cataract.

Figure 10:
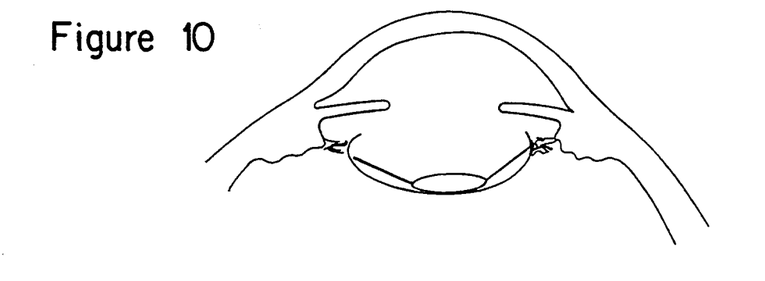
FIG. 10 shows an IOL according to the invention seated in the lens capsule.
Figure 11:
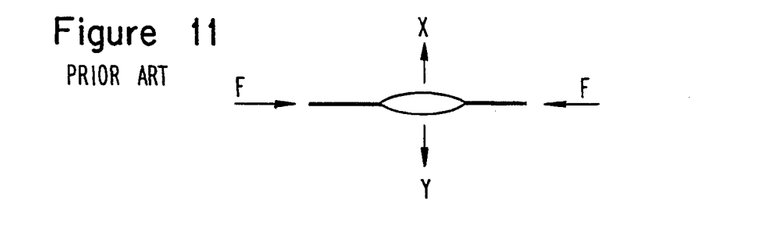
FIG. 11 shows a conventional IOL under force conditions.
Figure 12:
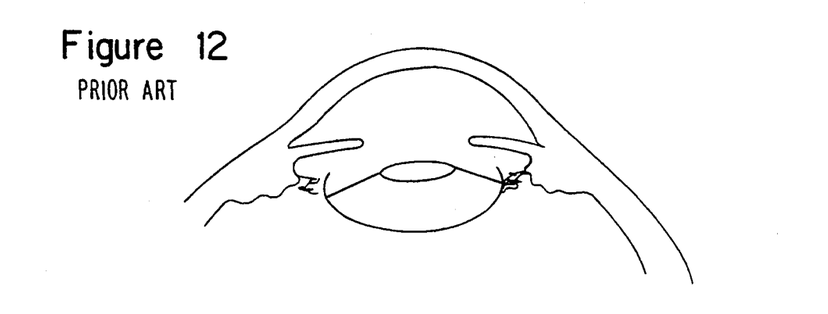
FIG. 12 shows a conventional IOL under force in the lens capsule.

If an ordinary IOL is made in the usual way but with a zero degree of angulation (see FIG. 11) and the haptics are compressed under force conditions (F) that are similar to those which exist during implantation in the capsule, the lens does not "vault" at all if the haptics are rigid enough or might move or "vault" in either direction X or Y depending upon very slight additional forces or torques by the person doing the compressing. If the lens vaults in a direction away from the posterior wall of the capsule (see FIG. 12) this would be quite unsatisfactory. It would therefore clearly be desirable to produce an IOL that when implanted in the posterior wall of the capsule would consistently vault in a predetermined direction, namely toward the posterior wall of the capsule (as shown in FIG. 10) and not away from the posterior wall of the capsule (as shown in FIG. 12).

We have discovered that an IOL can be produced which will initially have a zero degree of angulation but which due to compressive forces acting on the haptics during implantation in the capsule will consistently vault the optics against the posterior wall of the capsule and at a predetermined degree of angulation. We have found that the key to producing such an IOL is carefully structuring at least one segment of at least one haptic so that when that haptic is subjected to a compressive force that segment will create a torque which will vault the lens in a predetermined direction.

When our lens is seated in the capsule and the haptics are compressed by the sides of the capsule so as to keep the lens in the proper position, the optical part of the lens moves posteriorly, away from the iris, gaining contact with the posterior capsule wall. This movement of the optics creating an angle between the plane of the optics and haptic is often referred to as "vault" and this term is used in this patent application. The contact between the lens and the posterior segment of the capsule is believed to play an important role in reducing the risks for secondary cataract.

A characterizing feature oil the present invention is that when the haptics are compressed under conditions similar to implantation the lens gets a desired and controlled vault. This means that the direction of the vault as well as the resulting angulation is a predetermined characteristic of the lens. The advantage is illustrated in FIG. 10 which shows the lens implanted in the eye.

Figure 13:
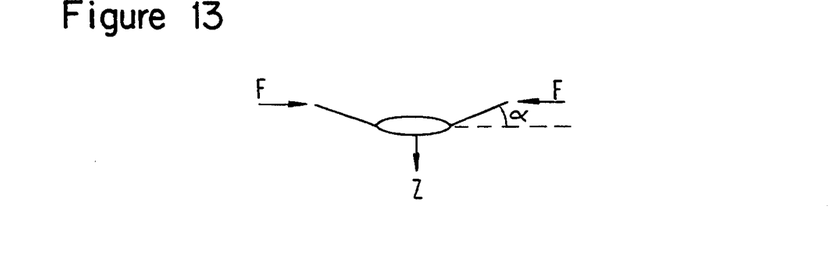
FIG. 13 shows an IOL according to the invention under compression.

FIG. 13 shows what happens when a lens according to our invention is compressed. When a compressive force F acts on the lens, that is to say when the lens is compressed under conditions similar to implantation, the optic body moves (i.e. the lens vaults) in a predefined desired direction Z resulting in an angulation α. This controlled and predetermined angulation will take place if the compressive force is greater than zero. If a prior art lens was made without a segment to impart torque and it was compressed, the optic body might move in the z-direction but with equal likelihood it might move in the opposite direction. The movement (vault) in such a case is uncontrolled and could not be relied upon by eye surgeons to produce a satisfactory result.

Figure 14:
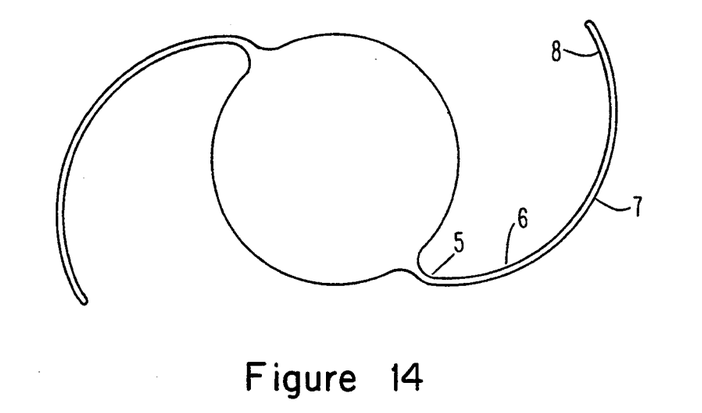
FIG. 14 shows an IOL according to the invention.
Figure 15:
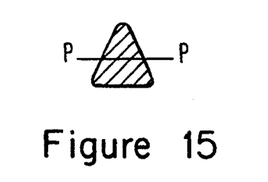
FIG. 15 shows a cross-section of a haptic according to a first embodiment.
Figure 16:
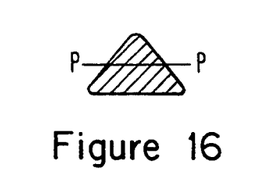
FIG. 16 shows a cross-section of a haptic according to a second embodiment.
Figure 17:
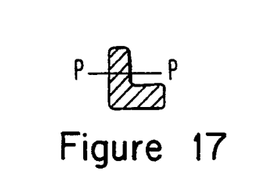
FIG. 17 shows a cross-section of a haptic according to a third embodiment.
Figure 18:
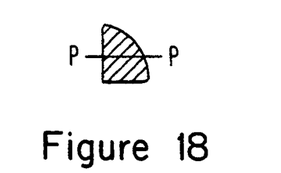
FIG. 18 shows a cross-section of a haptic according to a fourth embodiment.

One embodiment of our invention is shown in FIG. 14. It comprises a lens with two haptics each haptic comprising a connecting member 5 having a rectangular cross-section, a section 6 in which the cross-section gradually changes from rectangular to triangular, a section 7 of triangular cross-section and a section 8 in which the triangular cross-section gradually changes to a rectangular cross-section and which can optionally evolve into a rounded form at the end of the haptic. When a compressive force is applied to the haptics the segment that has a triangular cross section will create a torque or torsional force which will cause the lens to move or vault in a predetermined direction and assume a predetermined degree of angulation.

When haptics or portions thereof have a non-symmetrical cross-section as exemplified by FIGS. 15–18 it has been found that a sufficient torque results after compression to cause the predetermined direction of vaulting. Other cross-sections may also be suitable, as can be determined by a simple testing procedure. So can for instance the model showed in FIG. 18 be modified by removing material at the corner, for instance as defined by a quarter-circle concentric with the quarter-circle shown in the figure. It appears that as long as a portion of a haptic has a cross-section that is not symmetrical with respect to a plane passing through the center of both the lens and haptics (P—P in FIGS. 15–18) a torque force will be generated when the haptic is subjected to a compressive force, such torque force causing the lens to vault in only one predetermined direction and angulation.

Figure 19:
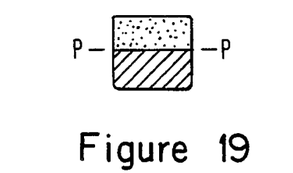
FIG. 19 shows a cross-section of a haptic according to a fifth embodiment.

In another embodiment of the invention the loops are each composed of two different materials having different stiffness. This is illustrated in FIG. 19 which shows the cross-section of such a haptic. In the specific case illustrated in FIG. 19 the thickness of both materials is the same but the thickness could of course be different depending on the two materials used. The material are chosen so that a compressive force applied as described above gives a resultant torque which makes the lens vault in a desired way.

Figure 20:
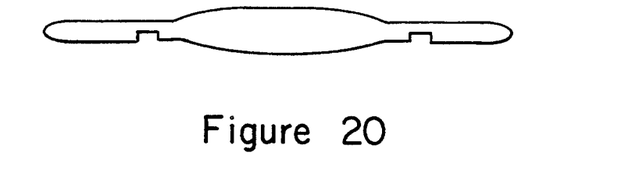
FIG. 20 shows an IOL according to a sixth embodiment.

In still another embodiment of the invention (FIG. 20) each of the haptics has one or more recess which can also result in an overall torque not equal to zero and hence the lens vaults when compressed under conditions similar to implantation.

It is readily appreciated that a great number of variations are available for utilising the basic concept of the present invention. So can for instance the length of the various haptic sections be varied as well.

A lens according to the invention has been found to make the insertion through a tunnel/valve more safe and easy to carry on than does a conventional IOL such as shown in FIG. 5.

Although the IOL according to our invention has about a zero degree of angulation, we feel that an IOL having even a small negative degree of angulation would also have advantages over an IOL having a positive degree of angulation (i.e. shown in FIG. 5).

Intraocular lenses with haptics having a non-symmetrical cross-section as described above have been found to have an additional advantage in that such haptics are much easier to see during implantation. It need not to be said that it is essential that, when the surgeon manoeuvres the lens into the bag behind iris, he can see the haptics to be able to put them into the correct position in the capsular bag. For this reason there are lenses having coloured haptics, a characteristic which is easy to achieve when making three-piece lenses, but much more difficult when the whole lens is prepared in one piece from a lens blank.

A prior art one-piece lens has haptics with substantially rectangular or quadratic cross-sections which are difficult to see during surgery. The optical characteristics (reflection/refraction) of a haptic with non-symmetrical cross-sections as described above are different which makes the haptic easy to see and to follow during insertion into the capsule. This characteristic accordingly makes the implantation much more convenient and safe.

This advantage can be utilized also in cases when it is not required that the lens should vault in response to a compressive force acting on the haptics. So can a lens with angulated haptics be provided with haptic segments having a non-symmetrical cross-section which makes the haptics easy to see in the eye. In this case vaulting is not required or even desirable and said segments should then be designed to give an overall torque equal to zero. This can for instance be achieved by one segment having a torque in direction X followed by one segment having an equal torque in the opposite direction Y (compare FIG. 11). The number of segment can of course be increased but the overall torque should be zero.

I claim:

1. Intraocular lens that includes an optical lens body defined by a plane and haptics extending outwardly from said optical lens body the improvement comprising that when said haptics are not under compression they extend at about a zero degree of angulation with respect to said plane of the lens body and that at least one of said haptics has at least one segment which is formed so that upon compression of the haptics under conditions similar to implantation said at least one segment will convert said compression to a torque which causes the lens to vault in only one predetermined direction and to a predetermined angulation greater than zero.

2. An intraocular lens according to claim 1 wherein said segment has a non-symmetrical cross-section.

3. An intraocular lens according to claim 2 wherein said segment has a triangular cross-section.

4. An intraocular lens according to claim 2 wherein said segment has a L-shaped cross-section.

5. An intraocular lens according to claim 2 wherein said segment has a cross-section corresponding to a quarter-circle.

6. An intraocular lens according to claim 1 wherein said segment is composed of two materials having different stiffness.

7. An intraocular lens that includes an optical body and at least two haptics for fixation of the lens in the eye wherein at least one of said haptics comprises a connecting member to the lens having a rectangular cross-section, an adjoining section in which the cross-section gradually changes from rectangular to triangular, a next adjoining section of triangular cross-section and a next adjoining section in which the triangular cross-section gradually changes to a rectangular cross-section that evolves into a rounded form at the end of the haptic.

* * * * *

(12) EX PARTE REEXAMINATION CERTIFICATE (6327th)
United States Patent
Jansen (10) Number: US 5,376,115 C1
(45) Certificate Issued: Jul. 29, 2008

(54) INTRAOCULAR LENS WITH VAULTING HAPTIC (75) Inventor: Peter Jansen, Uithuizen (NL)

(73) Assignee: AMO Groningen B.V., Groningen (NL)

Reexamination Request:
No. 90/008,535, Apr. 18, 2007

Reexamination Certificate for:
Patent No.: 5,376,115
Issued: Dec. 27, 1994
Appl. No.: 08/099,333
Filed: Aug. 2, 1993

(51) Int. Cl.
*A61F 2/16* (2006.01)

(52) U.S. Cl. ...................................................... 623/6.49
(58) Field of Classification Search .................. None
See application file for complete search history.

(56) References Cited

U.S. PATENT DOCUMENTS

| 4,159,546 | A | 7/1979 | Shearing |
| 4,244,060 | A | 1/1981 | Hoffer |
| 4,268,921 | A | 5/1981 | Kelman |
| 4,316,293 | A | 2/1982 | Bayers |
| 4,343,050 | A | 8/1982 | Kelman |
| 4,403,353 | A | 9/1983 | Tennant |
| 4,502,162 | A | 3/1985 | Gerhardt |
| 4,502,163 | A | 3/1985 | Graham |
| 4,524,468 | A | 6/1985 | Kelman |
| RE31,963 | E | 8/1985 | Kelman |
| 4,573,998 | A | 3/1986 | Mazzocco |
| 4,576,607 | A | 3/1986 | Kelman |
| 4,578,078 | A | 3/1986 | Arkell |
| 4,624,670 | A | 11/1986 | Bechert |
| 4,634,442 | A | 1/1987 | Link |
| 4,642,113 | A | 2/1987 | Dubroff |
| 4,648,878 | A | 3/1987 | Kelman |
| 4,676,792 | A | 6/1987 | Praeger |
| 4,702,244 | A | 10/1987 | Mazzocco |
| 4,704,123 | A | 11/1987 | Smith |
| 4,710,195 | A | 12/1987 | Giovinazzo |
| 4,725,277 | A | 2/1988 | Bissonette |
| 4,726,367 | A | 2/1988 | Shoemaker |
| 4,787,902 | A | 11/1988 | Sheets |
| 4,790,845 | A | 12/1988 | Grendahl |
| 4,834,749 | A | 5/1989 | Orlosky |
| 4,863,464 | A | 9/1989 | Dusek |
| 4,863,465 | A | 9/1989 | Kelman |
| 4,871,362 | A | 10/1989 | Nurmamedov |
| 4,932,967 | A | 6/1990 | Kansas |
| 4,969,897 | A | 11/1990 | Kalb |
| 4,990,159 | A | 2/1991 | Kraft |

(Continued)

FOREIGN PATENT DOCUMENTS

| DE | 3607042 | 9/1986 |
| EP | 0145112 | 1/1988 |
| EP | 0278724 | 8/1988 |
| EP | 0091242 | 9/1988 |
| EP | 0137590 | 12/1988 |

(Continued)

OTHER PUBLICATIONS

"Peripheral Anterior Synechia Overlying The Haptics Of Posterior Chamber Lenses"; Ophthalmology, vol. 97, No. 4, Publication Date Apr. 1990, pp. 415–423.

(Continued)

*Primary Examiner*—Jeffrey R Jastrzab (57) ABSTRACT

An intraocular lens that includes an optical lens body and haptics extending outwardly from the optical lens, said haptics extending at about a zero degree of angulation with respect to the lens body when not under compression and at least one haptic having at least one segment which is formed so that upon compression of the haptics under conditions similar to implantation said at least one segment will create a torque which causes the lens to vault in only one predetermined direction and to a predetermined angulation greater than zero.

U.S. PATENT DOCUMENTS

| | | |
|---|---|---|
| 5,071,432 A | 12/1991 | Baikoff |
| 5,074,942 A | 12/1991 | Kearns |
| 5,133,749 A | 7/1992 | Nordan |
| 5,160,345 A | 11/1992 | Bragg |
| 5,197,981 A | 3/1993 | Southard |
| 5,217,491 A | 6/1993 | Vanderbilt |
| RE34,424 E | 10/1993 | Walman |
| 5,282,855 A | 2/1994 | Bragg |
| 5,306,297 A | 4/1994 | Rheinish |
| 5,336,262 A | 8/1994 | Chu |

FOREIGN PATENT DOCUMENTS

| | | |
|---|---|---|
| EP | 0325297 | 7/1989 |
| EP | 0215468 | 12/1989 |
| EP | 0177143 | 3/1990 |
| EP | 0404478 | 12/1990 |
| EP | 0255759 | 9/1991 |
| EP | 0496022 | 7/1992 |
| EP | 0566461 | 10/1993 |
| FR | 2675991 | 11/1992 |
| GB | 02118841 | 11/1983 |
| WO | WO 85/02995 | 7/1985 |
| WO | WO 94/05233 | 3/1994 |

OTHER PUBLICATIONS

"Anterior Chamber Lenses"; J Catatact Refract Surg, vol. 13, No. 2, Publication date Mar. 1987, pp. 157–174.

"Simplified Insertion Technique For the SI–26NB Intraocular Lens"; J Catatact Refract Surg, vol. 18, No. 6, Publication date Nov. 1992, pp. 619–622.

"Anatomic Study of Transsclerally Sutured Intracular Lens Implantation"; Am J Ophthalmol, vol. 108, No. 3, Publication date Sep. 15, 1989, pp. 300–309.

"A short Haptic Diameter Modified J–loop Intraocular Lens For Improved Capsular Bag Performance"; J Catatact Refract Surg, vol. 14, No. 2, Publication date Mar. 1988, pp. 161–166.

"High–Speed Photographic Evaluation Of Intracular Lens Movements"; Am J Ophthalmol, vol. 97, No. 6, Publication date Jun. 84, 1989, pp. 752–759.

"The ONG Capsular Lens, Report of 100 Implantations"; Doc Ophthalmol, vol. 52, No. 3–4, Publication date Jan. 29, 1982, pp. 355–361.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1 and 3–7 are determined to be patentable as amended.

New claim 8 is added and determined to be patentable.

1. Intraocular lens that includes an optical lens body defined by a plane and haptics extending outwardly from said optical lens body the improvement comprising that when said haptics are not under compression they extend at about a zero degree of angulation with respect to said plane of the lens body and that at least one of said haptics has at least one segment which is formed so that upon compression of the haptics under conditions similar to implantation said at least one segment will convert said compression to a torque which causes the lens to vault in only one predetermined direction and to a predetermined angulation greater than zero, *wherein said at least one segment has a non-symmetrical cross-section and wherein said at least one haptic has a proximal end and a distal end, the proximal end attached to the lens body and each haptic extending from the lens body such that the distal end of each haptic is not attached to the lens body.*

3. An intraocular lens according to claim [2] *1* wherein said segment has a triangular cross-section.

4. An intraocular lens according to claim [2] *1* wherein said segment has a L-shaped cross-section.

5. An intraocular lens according to claim [2] *1* wherein said segment has a cross-section corresponding to a quarter-circle.

6. [An intraocular] *Intraocular* lens [according to claim 1] *that includes an optical lens body defined by a plane and haptics extending outwardly from said optical lens body the improvement comprising that when said haptics are not under compression they extend at about a zero degree of angulation with respect to said plane of the lens body and that at least one of said haptics has at least one segment which is formed so that upon compression of the haptics under conditions similar to implantation said at least one segment will convert said compression to a torque which causes the lens to vault in only one predetermined direction and to a predetermined angulation greater than zero and* wherein said segment is composed of two materials having different stiffness.

7. An intraocular lens that includes an optical body and at least two haptics *being each attached to the body only at one end of each haptic,* for fixation of the lens in the eye wherein at least one of said haptics comprises a connecting member to the lens having a rectangular cross-section, an adjoining section in which the cross-section gradually changes from rectangular to triangular, a next adjoining section of triangular cross-section and a next adjoining section in which the triangular cross-section gradually changes to a rectangular cross-section that evolves into a rounded form at the end of the haptic, *so that upon compression of the haptics under conditions similar to implantation said at least one haptic will convert said compression to a torque which causes the lens to vault in only one predetermined direction and to a predetermined angulation greater than zero.*

8. *An intraocular lens according to claim 1, wherein the at least one segment has a cross section and wherein the cross section has an anterior surface width and a posterior surface width along the same cross section, said cross section taken generally along a plane parallel to the optic axis of the lens, the anterior surface width and the posterior surface width are unequal.*

* * * * *